United States Patent
Li

(10) Patent No.: US 8,213,693 B1
(45) Date of Patent: Jul. 3, 2012

(54) SYSTEM AND METHOD TO TRACK AND NAVIGATE A TOOL THROUGH AN IMAGED SUBJECT

(75) Inventor: Dun Alex Li, Salem, NH (US)

(73) Assignee: General Electric Company, Schenectady, NY (US)

( * ) Notice: Subject to any disclaimer, the term of this patent is extended or adjusted under 35 U.S.C. 154(b) by 1280 days.

(21) Appl. No.: 11/860,368

(22) Filed: Sep. 24, 2007

Related U.S. Application Data

(60) Provisional application No. 60/938,385, filed on May 16, 2007.

(51) Int. Cl.
*G06K 9/00* (2006.01)
*A61N 5/00* (2006.01)

(52) U.S. Cl. ........ 382/128; 600/407; 600/423; 600/424; 600/437

(58) Field of Classification Search ............. 382/128; 600/407, 423, 424, 437
See application file for complete search history.

(56) References Cited

U.S. PATENT DOCUMENTS

| | | | |
|---|---|---|---|
| 4,706,681 A | 11/1987 | Breyer et al. | |
| 4,821,731 A | 4/1989 | Martinelli et al. | |
| 4,896,673 A | 1/1990 | Rose et al. | |
| 5,135,001 A | 8/1992 | Sinofsky et al. | |
| 5,840,025 A * | 11/1998 | Ben-Haim | 600/424 |
| 5,928,248 A * | 7/1999 | Acker | 623/1.11 |
| 5,938,602 A | 8/1999 | Lloyd | |
| 6,368,285 B1 * | 4/2002 | Osadchy et al. | 600/508 |
| 6,490,474 B1 | 12/2002 | Willis et al. | |
| 6,514,249 B1 | 2/2003 | Maguire et al. | |
| 6,618,612 B1 * | 9/2003 | Acker et al. | 600/424 |
| 6,669,635 B2 | 12/2003 | Kessman et al. | |
| 6,716,166 B2 | 4/2004 | Govari | |
| 6,719,700 B1 * | 4/2004 | Willis | 600/462 |
| 6,773,402 B2 | 8/2004 | Govari et al. | |
| 6,776,402 B2 | 8/2004 | Miyamoto et al. | |
| 6,892,091 B1 * | 5/2005 | Ben-Haim et al. | 600/509 |
| 7,090,639 B2 | 8/2006 | Govari | |
| 7,156,816 B2 | 1/2007 | Schwartz et al. | |
| 7,327,872 B2 * | 2/2008 | Vaillant et al. | 382/154 |
| 7,366,562 B2 * | 4/2008 | Dukesherer et al. | 600/424 |
| 7,499,743 B2 * | 3/2009 | Vass et al. | 600/426 |
| 7,505,810 B2 * | 3/2009 | Harlev et al. | 600/509 |

(Continued)

OTHER PUBLICATIONS

Kanckstedt, C. et al, "Semi-automated 3-dimensional intracardiac echocardiography: development and initial clinical experience of a new system to guide ablation procedures", Heart Rhythm, 3 (12), pp. 1453-1459, 2006.

(Continued)

*Primary Examiner* — David A Vanore

(57) ABSTRACT

A system to navigate an imaged subject in relation to an acquired image of the imaged subject is provided. The system includes an intracardiac echocardiography (ICE) imaging system having a transducer operable to acquire image data so as to create a four-dimensional image model of the imaged subject. The model is defined in spatial relation and orientation relative to an image coordinate system. A tracking system is operable to track movement and orientation of the transducer through the imaged subject relative to a tracking coordinate system. A controller is electrically connected in communication with the imaging system and the tracking system. The controller is operable to register the image coordinate system with the tracking coordinate system, and to calibrate the image coordinate system and the tracking coordinate system relative to a common reference having fiducials of known spatial relation.

19 Claims, 5 Drawing Sheets

U.S. PATENT DOCUMENTS

| | | | | |
|---|---|---|---|---|
| 7,515,954 | B2 * | 4/2009 | Harlev et al. | 600/509 |
| 7,599,730 | B2 * | 10/2009 | Hunter et al. | 600/424 |
| 7,660,623 | B2 * | 2/2010 | Hunter et al. | 600/424 |
| 7,697,972 | B2 * | 4/2010 | Verard et al. | 600/424 |
| 7,713,210 | B2 * | 5/2010 | Byrd et al. | 600/459 |
| 7,729,752 | B2 * | 6/2010 | Harlev et al. | 600/509 |
| 7,751,868 | B2 * | 7/2010 | Glossop | 600/426 |
| 7,787,951 | B1 * | 8/2010 | Min | 607/17 |
| 7,912,258 | B2 * | 3/2011 | Warmath et al. | 382/128 |
| 7,918,793 | B2 * | 4/2011 | Altmann et al. | 600/437 |
| 7,930,018 | B2 * | 4/2011 | Harlev et al. | 600/509 |
| 7,937,136 | B2 * | 5/2011 | Harlev et al. | 600/509 |
| 7,953,475 | B2 * | 5/2011 | Harlev et al. | 600/509 |
| 7,957,791 | B2 * | 6/2011 | Harlev et al. | 600/509 |
| 2002/0005719 | A1 | 1/2002 | Gilboa et al. | |
| 2002/0026118 | A1 | 2/2002 | Govari | |
| 2002/0042571 | A1 | 4/2002 | Gilboa et al. | |
| 2003/0013958 | A1 | 1/2003 | Govari et al. | |
| 2003/0074011 | A1 | 4/2003 | Gilboa et al. | |
| 2003/0208102 | A1 | 11/2003 | Gilboa | |
| 2004/0102769 | A1 | 5/2004 | Schwartz et al. | |
| 2004/0138548 | A1 | 7/2004 | Strommer et al. | |
| 2004/0162507 | A1 | 8/2004 | Govari | |
| 2004/0162550 | A1 | 8/2004 | Govari et al. | |
| 2004/0254458 | A1 | 12/2004 | Govari | |
| 2005/0197557 | A1 | 9/2005 | Strommer et al. | |
| 2006/0241445 | A1 | 10/2006 | Altmann et al. | |
| 2006/0253024 | A1 | 11/2006 | Altmann et al. | |
| 2006/0253029 | A1 | 11/2006 | Altmann et al. | |
| 2006/0253030 | A1 | 11/2006 | Altmann et al. | |
| 2006/0253031 | A1 | 11/2006 | Altmann et al. | |
| 2006/0253032 | A1 | 11/2006 | Altmann et al. | |
| 2007/0167821 | A1 | 7/2007 | Lee et al. | |
| 2011/0190629 | A1 * | 8/2011 | Guenther et al. | 600/437 |

OTHER PUBLICATIONS

Proulx, T.L. et al, "Advances in Catheter-Based Ultrasound Imaging", IEEE International Ultrasonics Symposium Proceedings, 2005.

Huang, X. et al, "Dynamic 3D Ultrasound and MR Image Registration of the Beating Heart", MICAI, LNCS 3750, pp. 171-178, 2005.

Martin, R. et al, "A Miniature Position and Orientation Locator for Three Dimensional Echocardiography", IEEE Proceedings on Computer in Cardiology, pp. 25-28, 1993.

Leotta, D. F. et al, "Three-Dimensional Ultrasound Imaging Using Multiple Magnetic Tracking Systems and Miniature Magnetic Sensors", IEEE on Ultrasonics Symposium, pp. 1415-1418, 1995.

Pagoulatos, N. et al, "Interactive 3-D Registration of Ultrasound and Magnetic Resonance Images Based on a Magnetic Position Sensor", IEE on Info. Tech. In Biomedicine, vol. 3, No. 4, 1999.

"Catheter Ablation", Cleveland Clinic—Heart & Vascular Institute, http:/www.clevelandclinic.org/heartcenter/pub/guide/tests/procedures/ablation.htm, Apr. 2005.

* cited by examiner

SYSTEM AND METHOD TO TRACK AND NAVIGATE A TOOL THROUGH AN IMAGED SUBJECT

RELATED APPLICATIONS

This application claims priority to Provisional Application No. 60/938,385 filed on May 16, 2007, and is hereby incorporated herein by reference in its entirety.

BACKGROUND OF THE SUBJECT MATTER

The subject matter herein generally relates to a medical imaging, and more specifically, to a system and method to navigate a tool through an imaged subject.

Image-guided surgery is a developing technology that generally provides a surgeon with a virtual roadmap into a patient's anatomy. This virtual roadmap allows the surgeon to reduce the size of entry or incision into the patient, which can minimize pain and trauma to the patient and result in shorter hospital stays. Examples of image-guided procedures include laparoscopic surgery, thoracoscopic surgery, endoscopic surgery, etc. Types of medical imaging systems, for example, computerized tomography (CT), magnetic resonance imaging (MRI), positron emission tomography (PET), ultrasound (US), radiological machines, etc., can be useful in providing static image guiding assistance to medical procedures. The above-described imaging systems can provide two-dimensional or three-dimensional images that can be displayed to provide a surgeon or clinician with an illustrative map of an area of interest of a patient's body.

When performing a medical procedure, it is desired to calibrate or align the acquired image data of the imaged subject with the tracked tool so as to navigate through the imaged subject. Yet, the sensors to the track the tool and the detectors to acquire the image data may not be precisely located due to manufacturing variation.

BRIEF DESCRIPTION OF THE SUBJECT MATTER

There is a need for a system to track and navigate the position and movement of a surgical instrument or tool (e.g., a catheter) simultaneously relative to real-time generated images or models of the patient's anatomy. Generally, as a surgeon moves the medical instrument with respect to the patient's anatomy, virtual images of the instrument or object are displayed simultaneously relative to real-time acquired image data represented in the model of the patient's anatomy. The system and method of tracking should be able to readily track the spatial relationship of the medical instruments or objects traveling through an operating space of patient. The system and method should be able to compensate for manufacturing in the assembly of the sensors of the tracking system and the assembly of the detectors in the imaging system.

The above-mentioned need is addressed by the embodiments of the subject matter described herein in the following description.

According to one embodiment of the subject matter described herein, a system to navigate in an area of interest of an imaged subject in relation to an acquired image of the imaged subject is provided. The system includes an intracardiac echocardiography (ICE) imaging system having a transducer operable to acquire image data so as to create a four-dimensional image model of the imaged subject. The model is defined in spatial relation and orientation relative to an image coordinate system. The system also includes a tracking system operable to track movement and orientation of the transducer through the imaged subject relative to a tracking coordinate system. The system also includes a controller electrically connected in communication with the imaging system and the tracking system. The controller includes a processor operable to execute a plurality of program instructions stored in a memory, the plurality of program instructions in combination with the processor operable to register the image coordinate system with the tracking coordinate system; and to calibrate the image coordinate system and the tracking coordinate system relative to a common reference having a plurality of fiducials of known spatial relation.

According to yet another embodiment of the subject matter described herein, a method of navigating in an area of interest of an imaged subject is provided. The method comprises the acts of generating a four-dimensional model of the region of interest of the imaged subject with an intracardiac echocardiography (ICE) imaging system, the four-dimensional model including image data arranged in spatial relation and orientation relative to an image coordinate system and correlated relative to a time of acquisition; tracking movement and orientation of the transducer traveling through the imaged subject relative to a tracking coordinate system; registering the image coordinate system relative to the tracking coordinate system; and calibrating the image coordinate system and the tracking coordinate system relative to a common reference frame comprising a plurality of fiducials of known spatial relation.

According to yet another embodiment, a frame to calibrate an imaging system relative to a tracking system is provided. The imaging system includes a transducer operable to acquire image data of an imaged subject. The frame comprises a series of fiducials of known spatial relation relative to one another; and an adapter configured to receive the transducer of the imaging system. The adapter is configured to rotate with respect to the frame.

Systems and methods of varying scope are described herein. In addition to the aspects and advantages described in this summary, further aspects will become apparent by reference to the drawings and with reference to the detailed description that follows.

DETAILED DESCRIPTION OF THE SUBJECT MATTER

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
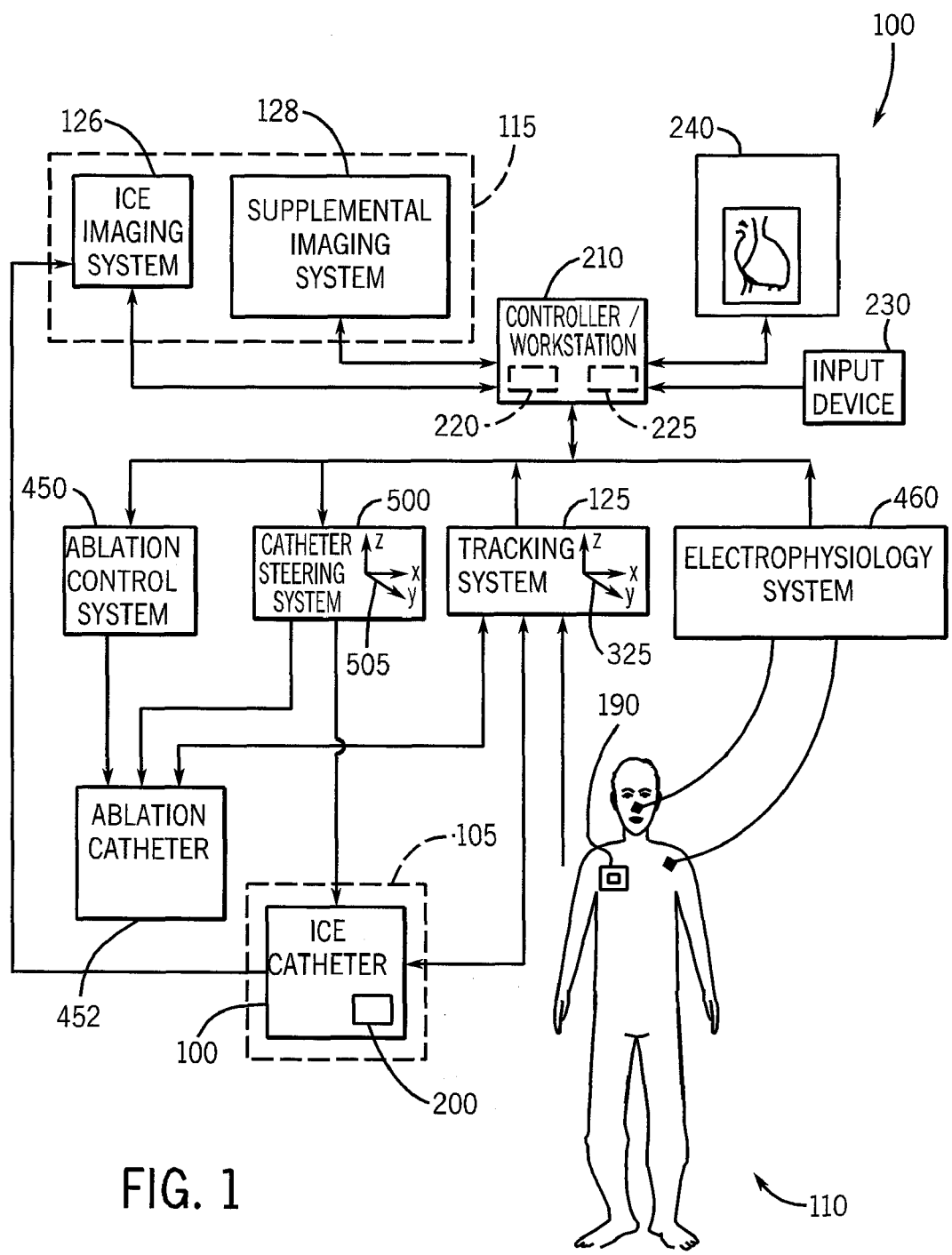
FIG. 1 illustrates a schematic diagram of an embodiment of a system of the subject matter described herein to perform imaged guided medical procedures on an imaged subject.

FIG. 1 illustrates an embodiment of a system 100 operable to track movement of a tool or object 105 through an anatomy of an imaged subject 110. The system 100 generally includes an image acquiring system or device 115, and a tracking system 125 operable to track or monitor a position of the object or tool 105 traveling through the imaged subject 110.

The image acquiring system 115 is generally operable to generate a two-dimensional, three-dimensional, or four-dimensional image data corresponding to an area of interest of the imaged subject 110. Examples of the image acquiring system 115 can include, but is not limited to, computed tomography (CT), magnetic resonance imaging (MRI), x-ray or radiation, positron emission tomography (PET), computerized tomosynthesis (CT), ultrasound (US), angiographic, fluoroscopic, and the like or combination thereof. The image acquiring system 115 can be operable to generate static images acquired by static imaging detectors (e.g., CT systems, MRI systems, etc.) prior to a medical procedure, or real-time images acquired with real-time imaging detectors (e.g., angioplastic systems, laparoscopic systems, endoscopic systems, etc.) during the medical procedure. Thus, the types of images can be diagnostic or interventional.

An exemplary image acquiring system 115 includes a real-time, intracardiac echocardiography (ICE) imaging system 126 that employs ultrasound to acquire image data of the patient's anatomy and to merge acquired image data to generate a three-dimensional model of the patient's anatomy relative to time, generating herein referred to as a four-dimensional model or image. In accordance with another embodiment, the image acquiring system 115 is operable to fuse or combine acquired image data using above-described ICE imaging system 126 with pre-acquired image data or image models (e.g., two- or three-dimensional reconstructed image models) generated by another type of supplemental imaging system 128, examples of which are described above (e.g., CT, MRI, PET, etc.).

The tool or object 105 can be a surgical tool, navigational tool, a guidewire, a catheter, an endoscopic tool, a laparoscopic tool, ultrasound probe, pointer, aspirator, coil, or the like employed in a medical procedure (e.g., ablation of tissue). Yet, the type of tool 105 can vary.

Figure 3:
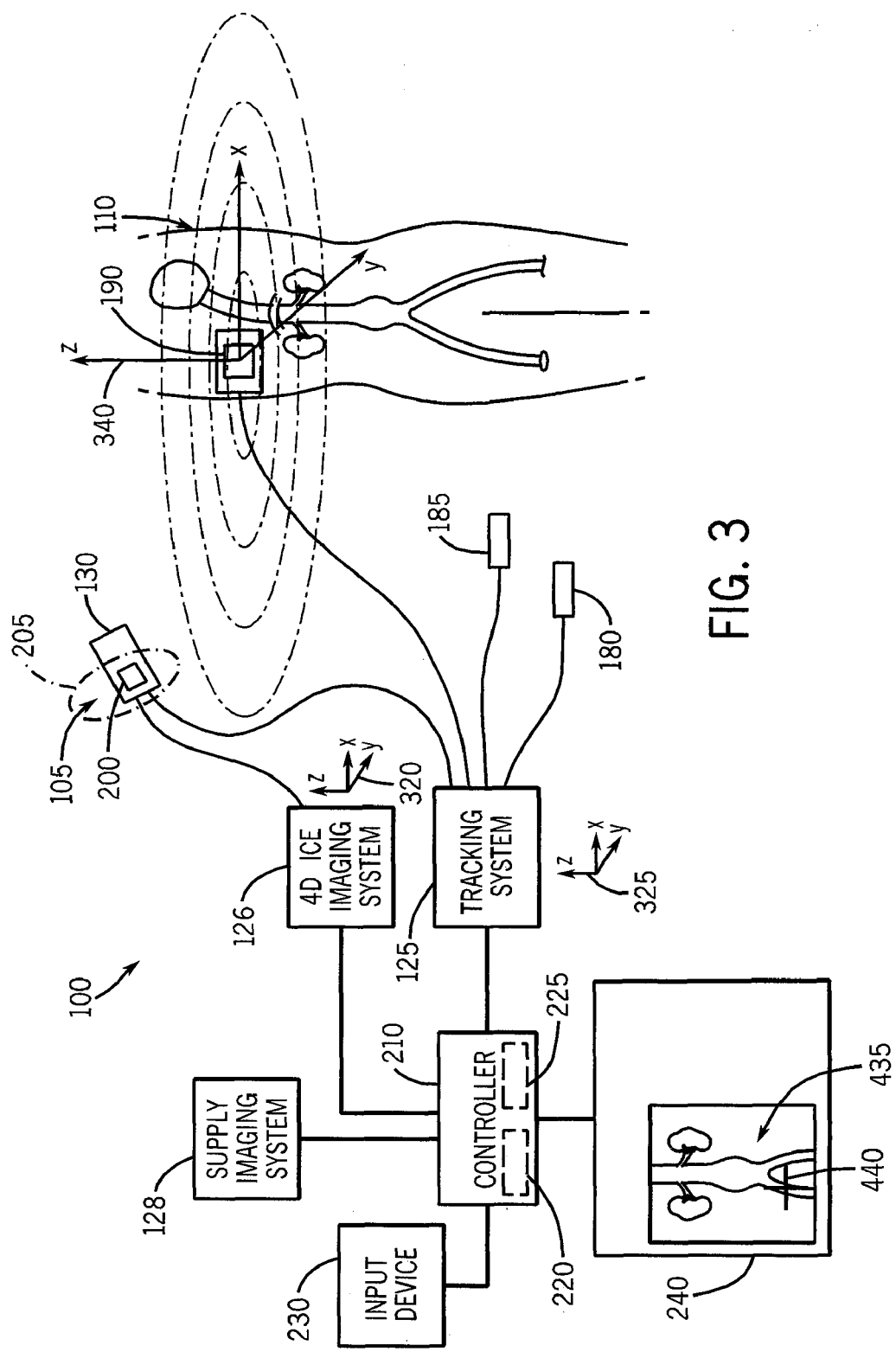
FIG. 3 illustrates a more detailed schematic diagram of a tracking system in combination with an imaging system as part of the system described in FIG. 1.

Referring to FIG. 3, an embodiment of the tool 105 operable to acquire intracardiac echocardiography (ICE) image data of the imaged subject 110 (See FIG. 1) includes an ICE catheter 130. The illustrated embodiment of the ICE catheter 130 includes a transducer array 132, a micromotor 134, a drive shaft or other mechanical connection 136 between the micromotor 134 and the transducer array 132, an interconnect 138, and a catheter housing 140.

According to the depicted embodiment, the micromotor 134 via the drive shaft 136 generally rotates the transducer array 132. The rotational motion of the transducer array 132, is controlled by a motor control 142 of the micromotor 134. The interconnect 138 generally refers to, for example, cables and other connections coupling so as to receive and/or transmit signals between the transducer array 132 with the ICE imaging system (shown in FIG. 1) 126. An embodiment of the interconnect 138 is configured to reduce its respective torque load on the transducer array 132 and the micromotor 134.

Figure 2:
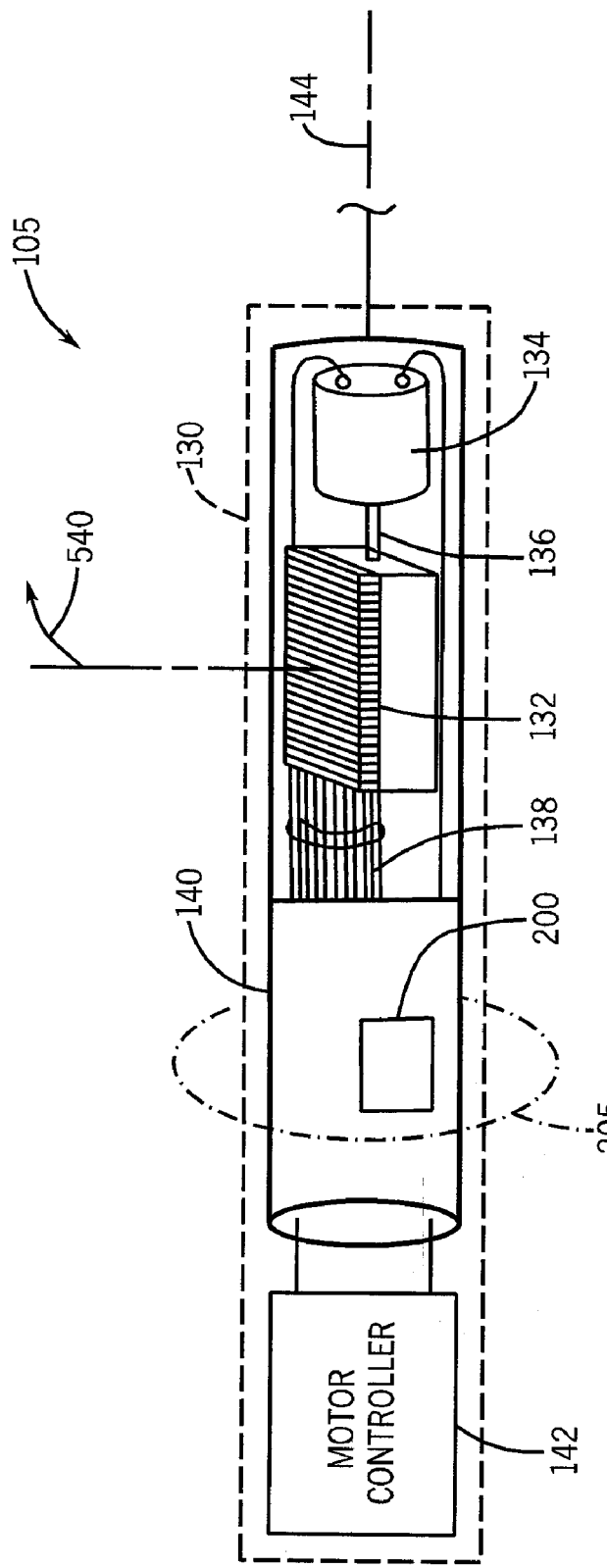
FIG. 2 illustrates a picture of a tool to travel through the imaged subject.

Still referring to FIG. 2, an embodiment of the catheter housing 140 generally encloses the transducer array 132, the micromotor 134, the drive shaft 136, the interconnect 138, and the motor control 142. The catheter housing is generally of a material, size, and shape adaptable to internal imaging applications and insertion into regions of interest of the imaged subject 110. At least a portion of the catheter housing 140 that intersects the ultrasound imaging volume or scanning direction is comprised of acoustically transparent (e.g., low attenuation and scattering, acoustic impedance near that of the blood and tissue ($Z \sim 1.5M$ Rayl) material. An embodiment of the space between the transducer array 132 and the housing 140 is filled with acoustic coupling fluid (e.g., water) having an acoustic impedance and sound velocity near those of blood and tissue (e.g., $Z \sim 1.5M$ Rayl, $V \sim 1540$ m/sec).

An embodiment of the transducer array 132 is a 64-element one-dimensional array having 0.110 mm azimuth pitch, 2.5 mm elevation, and 6.5 MHz center frequency. The elements of the transducer array 132 are electronically phased in order to acquire a sector image parallel to the longitudinal axis 144 of the catheter housing 140. In operation, the micromotor 134 mechanically rotates the transducer array 132 about the longitudinal axis 144. The rotating transducer array 132 captures a plurality of two-dimensional images for transmission to the ICE imaging system 126 (shown in FIG. 1). The ICE imaging system 126 is generally operable to assemble the sequence or succession of acquired two-dimensional images so as to generally produce or generate a three-dimensional image or reconstructed model of the imaged subject 110.

The rate of rotation of the transducer array 132 about the longitudinal axis 144 of the ICE catheter 130 is generally regulated by the motor control 142 via the micromotor 132. For example, the motor control 142 instructs the micromotor 134 to rotate the transducer array 132 relatively slowly to produce a three-dimensional reconstructed image. In contrast, the motor control 142 instructs the micromotor 134 to rotate the transducer array 132 relatively faster to produce a real-time three-dimensional reconstructed image, referred to as a four-dimensional image correlated to a general instantaneous time. The motor control 142 is also generally operable to vary the direction of rotation sous to generally create an oscillatory motion of the transducer array 132. In this manner, the torque load associated with the interconnect 138 is reduced such that the transducer array 132 can focus on imaging specific regions within the range of motion about the longitudinal axis 144.

Referring now to FIGS. 1 and 3, the tracking system 125 is generally operable to track or detect the position of the tool 105 and the ICE catheter 130 relative to the acquired image generated by the image acquiring system 115. As illustrated in FIG. 3, an embodiment of the tracking system 125 includes an array or series of sensors or tracking elements 180, 185, and 190 connected (e.g., via a hard-wired or wireless connection) to communicate position data to a controller (See FIG. 1). Yet, it should be understood that the number of tracking elements 180, 185, and 190 can vary. For sake of example, assume the tracking elements 180, 185, and 190 includes transmitters or dynamic references 180 and 185 in communication or coupled (e.g., RF signal, optically, electromagnetically, etc.) with one or more receivers 190. The number and combination of transmitters and receivers can vary. Either the transmitters 180 and 185 or the receiver 190 can define the reference of the spatial relation. An embodiment of the receiver 190 is detachably connected at and moves with a table in support of the imaged subject 110.

Referring now to FIGS. 1, 2 and 3, an embodiment of the tool 105 and ICE catheter 130 includes a tracking element 200 of the tracking system 125 in communication or coupled with the receiver 190. As shown in FIG. 2, an embodiment of the transmitter 200 generally includes a series of coils that define the orientation or alignment of the ICE catheter 130 about a rotational axis (generally aligned along the longitudinal axis 144) of the ICE catheter 130. Referring to FIG. 3, the transmitter 200 is located integrally with the ICE catheter 130 and is generally operable to generate or transmit a magnetic field 205 to be detected by the receiver 190 of the tracking system 125. In response to passing through the magnetic field 205, the receiver 190 generates a signal representative of a spatial relation and orientation relative to the transmitter 200. Yet, it should be understood that the type or mode of coupling, link or communication (e.g., RF signal, infrared light, magnetic field, etc.) operable to measure the spatial relation varies. The spatial relation and orientation of the transmitter 200 is mechanically defined and known in relation relative to a feature (e.g., a tip) of the ICE catheter 130. Thereby, the tracking system 125 is operable to track the position and orientation of the ICE catheter 130 navigating through the imaged subject 110. Alternatively, the receiver 190 can be attached at the ICE catheter 130 and in communication to measure a spatial relation with transmitters 180 or 185 located remote from the ICE catheter 130.

Alternatively, the transmitters 180, 185 or 200 can include a plurality of coils (e.g., Hemholtz coils) operable to generate a magnetic gradient field to be detected by the receiver 190 of the tracking system 125 and which defines an orientation of the ICE catheter 130. An embodiment of the receiver 190 includes at least one conductive loop operable to generate an electric signal indicative of spatial relation and orientation relative to the magnetic field generated by the transmitters 180, 185 and 200.

Still referring FIGS. 1, 2 and 3, a controller or workstation computer 210 is generally connected in communication with the imaging system 115 (e.g., the ICE imaging system 126 and static imaging system 128) and the tracking system 125. An embodiment of the controller 210 includes a processor 220 in communication with a memory 225. The processor 220 can be arranged independent of or integrated with the memory 225. The processor 220 is generally operable to execute the program instructions representative of acts described herein and stored in the memory 225. The processor 220 can also be capable of receiving input data or information or communicating output data. Examples of the processor 220 can include a central processing unit of a desktop computer, a microprocessor, a microcontroller, or programmable logic controller (PLC), or the like or combination thereof.

An embodiment of the memory 225 generally comprises one or more computer-readable mediums such as a hard disk, a floppy disk, CD, CD-ROM, DVD, compact storage medium, flash memory, random access memory, read-only memory, programmable read-only memory, memory stick, or the like or combination thereof. The memory 225 is operable to store the plurality of program instructions for execution by the processor 220. The memory 225 is also operable to store data generated or received by the controller 210.

The controller 210 further includes or is in communication with an input device 230 and output device 240. The input device 230 is generally operable to receive and communicate information data from user to the controller 210. The input device 230 can include a mouse device, pointer, keyboard, touch screen, microphone, or other like device capable of receiving a user directive. The output device 240 is generally operable to illustrate output data for viewing by the user. An embodiment of the output device 240 is operable to simultaneously illustrate or fuse static or real-time image data generated by the image acquiring system 115 (e.g., the ICE imaging system 126 and static imaging system 128) with tracking data generated by the tracking system 125. The output device 240 is capable of illustrating two-dimensional, three-dimensional image and/or four-dimensional image data through shading, coloring, and/or the like. Examples of the output device 240 include a cathode ray monitor, a liquid crystal display (LCD) monitor, a touch-screen monitor, a plasma monitor, or the like or combination thereof.

Figure 4:
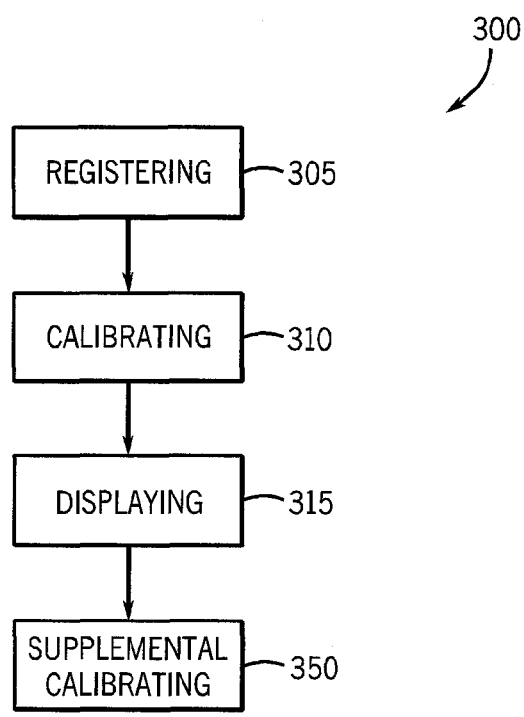
FIG. 4 illustrates a schematic diagram of a method of operating the system of FIG. 1.

Having provided a description of the general construction of the system 100, the following is a description of a method 300 (see FIG. 4) of operation of the system 100 in relation to the imaged subject 110. Although an exemplary embodiment of the method 300 is discussed below, it should be understood that one or more acts or steps comprising the method 300 can be omitted or added. It should also be understood that one or more of the acts can be performed simultaneously or at least substantially simultaneously, and the sequence of the acts can vary. Furthermore, it is embodied that at least several of the following acts can be represented as a series of modules of computer-readable program instructions to be stored in the memory 225 of the controller 210 for execution by the processor 220.

Referring now to FIG. 3 and for sake of example, assume that the spatial relation and orientation of the image data acquired by the transducer array 132 of the ICE imaging system 126 is defined by an image coordinate system 320 referenced in predetermined spatial relation and orientation relative to the transducer array 132 (See FIG. 2) at the ICE catheter 130. The image coordinate system 320 generally defines the spatial relation of voxels or pixels of image data relative to one another in the generated image frames or models generated by the ICE imaging system 126 in three-dimensions relative to time (i.e., four-dimensional image). Also, for sake of example, assume the tracking system 125 utilizes a tracking coordinate system 325 to define tracking spatial relation and orientation and movement of the tracking elements 180, 185, 190 and 200 relative to one another and to time. For example, the tracking coordinate system 325 references the orientation and spatial relation of the transmitter 200 at the ICE catheter 130 relative to the receiver or reference 190 of the tracking system 125. Although these coordinate systems 320 and 325 are described as Cartesian x-y-z coordinate systems, the type of coordinate systems 320 and 325 (e.g., polar, etc.) can vary. In addition, the location and orientation of the coordinate systems 320 and 325 can vary. Also assume that the spatial relation and orientation of the transmitter 200 relative to the ultrasonic transducer array 132 (See FIG. 2) is known or preoperatively measured.

Act 305 includes registering the image coordinate system 320 with the navigation or tracking coordinate system 325. Registering includes measuring (e.g., mechanically or optically) or calculating the spatial relation and orientation of the transmitter 200 relative to the transducer array 132 and in correlation relative to the image coordinate system 320. Registering act 305 further includes measuring the spatial relation and orientation of the transmitter 200 relative to the reference of the tracking coordinate system 325, which for sake of example assume is the tracking element 190 (e.g., receiver).

Act 310 includes calibrating the image coordinate system 320 of the image coordinate system 320 that defines the image data acquired by the transducer array 132 of the ICE imaging system 126 with the tracking image coordinate system 325 of the tracking system 125. An embodiment of the calibrating act or step 310 generally further includes an offline procedure of measuring a spatial relation and orientation of the image frames of data acquired by and relative to the ultrasonic transducer array 132 of the ICE imaging system 126.

Figure 5:
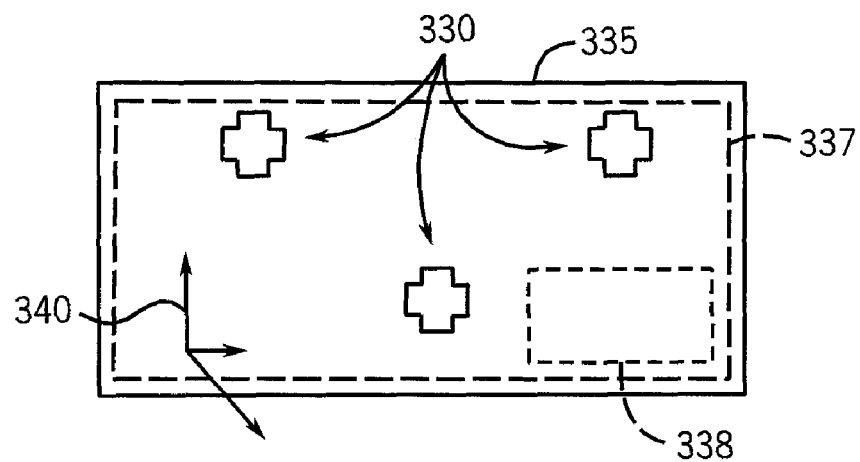
FIG. 5 illustrates a schematic diagram of an embodiment of a frame of fiducials to calibrate the imaging system with the tracking system in FIG. 3.

An embodiment of the offline calibrating act 310 includes pre-operatively applying or performing a rigid body transformation algorithm before acquiring images of the imaged subject 110 with the ICE imaging system 126. Referring now to FIG. 5, this embodiment of the calibrating act 310 includes acquiring image data of one or more ultrasonic fiducials 330 included in a phantom or ultrasonic lucent frame 335, in place of the imaged subject 110, with the ICE imaging system 126. An embodiment of the fiducials 330 are located at a predetermined spatial relationship and orientation with respect to one another. The arrangement, shape (e.g., cylinder, etc.) and dimensions of the fiducials 330 and the frame 335 can vary. The locations of the fiducials 330 and/or frame 335 are optimized to cover a field of view 337 of the ICE imaging system 126. The material of the ultrasound fiducials 330 is compatible to be detected with the ultrasound imaging technology. An embodiment of the frame 335 includes a docking area or station 338 configured to receive the ICE catheter 130 in a desired position or location and orientation relative to the fiducials 330 and frame 335.

The calibrating act 310 includes aligning acquired image data (e.g., grayscale, contrast, etc. of the pixels or voxels) of the fiducials 330 in the frame 335 as acquired by the transducer array 132 of the ICE catheter 130 and communicated to the ICE imaging system 126, with the physical or mechanical dimensions and orientation of the frame 335. The calibrating act 310 further includes measuring the mechanical spatial relation and orientation of the fiducials 330 in the frame 325 relative to ultrasonic transducer array 132 of the ICE imaging system 126 that acquires the image data of the fiducials 330. The manufacturer may provide predetermined measurements of the parameters that define the mechanical spatial relation and orientation of the fiducials 330 relative to the frame 335. Alternatively, the spatial relation and orientation of the fiducials 330 can be measured optically in accordance to conventional techniques associated with using a dual camera system. The predetermined spatial relationship can be communicated directly or indirectly and stored at the controller 210.

Referring to FIG. 3, with the tracking element 200 at the ICE catheter 130, one of the other tracking elements 180, 185 and 190 is fixedly or rigidly attached at the frame 335 and defines a reference or world coordinate system 340 that may or may not be the same as coordinate systems 320 and 325. The controller 210 calibrates the positions and orientations of the fiducials 330 (FIG. 5) with the world coordinate system 340. Yet another of the tracking elements 180, 185, and 190 is temporarily located or touched individually at each (or tracking elements are simultaneously located at all) of the fiducials 330. The controller 210 measures the spatial relation to calculate the positions and orientation of the tracking elements 180, 185, and 190 at each of the locations of the fiducials 330 (FIG. 5).

Referring to FIG. 5, the calibrating act or step 310 also includes acquiring image data of the fiducials 330 in the frame 335 with the transducer array 132 of the ICE imaging system 126. The controller 210 is operable to detect the location of the pixels or voxels having image data of the fiducials 330 in the generated image frames, and to measure the spatial relation and orientation of the pixels or voxels with image data of the fiducials 330 relative to one another.

Knowing the spatial relation of the tracking elements 180, 185, 190, and 200 relative to one another at the fiducials 330 as measured by the tracking system 125, and knowing the mechanical spatial relation and orientation of the fiducials 330 relative to the frame 335, the controller 210 is operable to automatically register the spatial relation and orientation of the fiducials 330 relative to the tracking coordinate system 325, and hence relative to the image coordinate system 320.

According to the above-described description, the controller 210 is operable to calibrate or to adjust calibration of the image coordinate system 320, the tracking coordinate system 325 and the world coordinate system 340 and registration relative to one another.

In yet another embodiment, the fiducials or markers or landmarks 330 can be integrated to include an additional tracking elements (transmitters or receivers or combination similar to tracking elements 180, 185, and 190) coupled in communication with the tracking system 125.

At least a portion of the above-described calibration act 310 can be represented as program instructions for execution by the processor 220 of the controller 210. Execution of the program instructions by the processor 220 can be triggered or controlled by a graphic user interface at the output device 140. The positions and orientations of the tracking elements 180, 185 or 190 touching the fiducials 330 can be denoted as T(f1 to wcs), T(f2 relative to wcs) through to T(fn relative to wcs), where T(fn relative to wcs) representative a position of each of the fiducials 330 (n) relative to the world coordinate system 340 as measured with the tracking system 125. The controller 210 processes the three-dimensional image data acquired with the ICE imaging system 126 to calculate the pixel or voxel position of the fiducials 330 illustrated in the three-dimensional data, denoted as T(fn relative ice), representative of the position and orientation of the fiducials 330 relative to the image coordinate system 320 that defines the three-dimensional model generated by the ICE imaging system 126. The position of the transmitter 200 and transducer array 132 at the ICE catheter 130, denoted as T(scs relative to wcs). The controller 210 executes the calibration through the following transformation algorithms:

$$T(\text{fi relative to } wcs) = T(\text{fi relative to } scs)T(scs \text{ relative to } wcs), \text{ and}$$

$$T(\text{fi relative to } scs) = T(\text{fi relative to } wcs)[T(scs \text{ relative to } wcs)].inv$$

where (fi) refers to the index (f1, ... fn) of fiducials 330, and T[scs relative to wcs].inv refers to the inverse transformation of T(scs relative to wcs). The controller 210 aligns the image frame generated by the ICE imaging system 126 with the position of the transmitter 200 at the ICE catheter 130 and frame 335 through the following transformations:

$$T(\text{fi relative to } scs) = T(\text{fi relative to ice})T(\text{ice relative to } scs), \text{ and}$$

$$T(\text{ice relative to } scs) = T(\text{fi relative to } scs)[T(\text{fi relative to ice})].inv$$

where (fi) refers to (f1, ... fn) index of fiducials 330, and [T(fi relative to ice)].inv denotes the inverse transformation of T(fi relative to ice). The calibration information denoted by T(ice relative to scs) can be stored in the memory or other computer-readable medium of the controller 210 or to the ICE imaging system 126.

As the tracking element 200 and transducer array 132 move with the ICE catheter 130 through the imaged subject 110, the tracking element 200 is linked in electromagnetic communication so as to allow the tracking system to track a location or movement of the tracking element 200 and attached transducer array 132 of the ICE catheter 130 relative to the other tracking elements 180, 185 and 190 and tracking coordinate system 325 for communication via a wireless or wired connection to the controller 200. Based on the signals from all or some of the tracking elements 180, 185, 190, 200, the controller 210 automatically continuously or periodically updates this measured spatial relation to track movement of the transducer array 132 at the ICE catheter 130 relative to the imaged subject 110 and acquired data represented in the four-dimensional model generated by the ICE imaging system 126.

The controller 210 is operable to track movement of the tool 105 or ICE catheter 130 via the tracking system 125 in accordance with known mathematical algorithms programmed as program instructions of a software for execution by the processor 220 of the controller 200. An exemplary navigation software is INSTATRAK® as manufactured by the GENERAL ELECTRIC® Corporation, and NAVIVISION® as manufactured by SIEMENS® and BRAINLAB®.

Act 315 includes displaying the tracked location of the tool 105 or ICE catheter 130 in spatial relation and orientation relative to and simultaneously with the four-dimensional reconstructed model generated by the ICE imaging system 126 for illustration at the output device 140 for viewing by the physician or clinician performing a medical procedure. It should be understood that the four-dimensional model generated by the ICE imaging system 126 can be combined, fused, or overlayed with various types of diagnostic, interventional, static, or real-time images generated by various examples of imaging systems 128 described above. As shown in FIG. 3, the virtual image 430 of the tool 105 or 130 in spatial relation to the four-dimensional model 435 generated by the ICE imaging system 126 can appear on one or more output devices 240 to guide the physician during delicate procedures. Various types of graphics, such as a cursor, triangle, square, cross-hairs, etc. can be used to illustrate a graphic virtual image (illustrated as cross-hairs and by reference 440) of the tool 105 or ICE catheter 130 in simultaneous illustration with the four-dimensional model 435 generated by the ICE imaging system 126. With the ability to track movement of the tool 105 or ICE catheter 130, the physician can more safely perform delicate procedures without damaging critical surrounding structures such as arteries and nerves that years ago would have been considered impossible.

Referring back to FIG. 1, having described calibration of the ICE imaging system 126 with the tracking system 125, act 350 of the method 300 and can be further extended to calibrating the ICE imaging system 126 and tracking system 125 with other components of the system 100, including an ablation catheter system 450, an electrophysiological system(s) (e.g., cardiac monitoring system, respiratory monitoring system, etc.) 460, and a steering system 500 of the ICE catheter 130.

An embodiment of the ablation system 450 having an ablation catheter 452 that is operable to work in combination with the ICE imaging system 126 to ablate or end electrical activity of tissue. An embodiment of an electrophysiological system(s) 460 is connected in combination with the ICE imaging system 126 is to track or monitor the cardiac cycle or respiratory cycle of imaged subject 110 correlated to the image data or three-dimensional models acquired or generated by the ICE imaging system 126. An embodiment of a catheter steering system 500 is generally operable to steer or drive movement and changes in direction of the ICE catheter 130 and attached transducer array 132 and transmitter 200 through the imaged subject 110. The steering system 500 can also be operable to drive rotation of the motor 134 in rotating or moving orientation of the transducer array 132 about the rotational axis 144. This embodiment of extending the calibrating act to a control system 500 is generally similar to the calibrating act described above directed to the ICE imaging system 126 with the tracking system 125.

Figure 6:
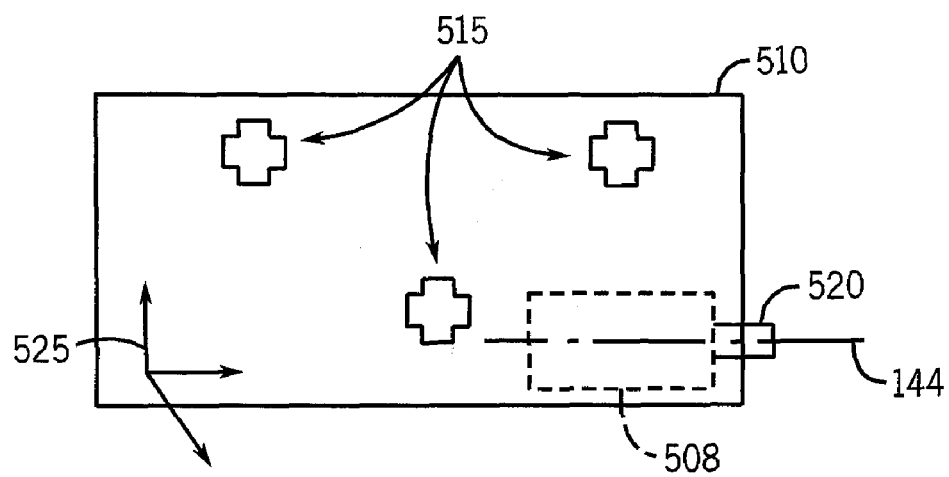
FIG. 6 illustrates a schematic diagram of another embodiment of a frame of fiducials that includes a docking station to receive the ICE catheter or other tool of FIG. 1.

For example, assume the spatial movement and orientation as recognized by the steering system 500 is defined by a steering coordinate system 505 (See FIG. 1). Referring now to FIG. 6, the ICE catheter 130 (See FIGS. 1, 2 and 3) can be placed at a docking station 508 (similar to the docking station 338 described above) on a frame 510 of fiducials 515. The docking station 508 includes an adapter 520 configured to receive the ICE catheter 130 or other tool 105. The adapter 520 of the docking station 508 is configured to rotate, or to allow rotation of the ICE catheter 130, about the longitudinal axis 144 (See FIG. 2) with respect to a remainder of the frame 510. A tracking element or sensor 180, 185, or 190 of the tracking system 125 is attached at the frame 510 to define the reference or world coordinate system 525, similar to the world coordinate system 340 described above. Alignment of the ICE imaging system 126 and the steering control system 500 includes measuring the angular displacement between the mechanical steering angle (e.g., as referenced by 540 in FIG. 2) of the motor 140 at the ICE catheter 130 or other drive device of the ICE catheter 130 relative to the orientation of the transmitter 200 at the ICE catheter 130. It should be understood that the reference (e.g., longitudinal axis 144, axis of motor, pivot point, etc.) and measured displacement (rotational, linear, pivot angle, etc.) tracked and adjusted by the steering system 500 could vary.

An embodiment of this extended calibrating act 350 can be represented in modules of computer readable programming instructions that can be launched from a graphic user interface at the output device. For example, assume the steering system 500 is operable to drive rotation of the ICE catheter 130 or motor 140 or transducer array 132 attached thereto among a plurality of angular positions herein referred to as T(mcs.a1 relative to wcs), T(mcs.a2 relative to wcs) . . . to T(mcs.an relative to wcs), where a1, . . . an represent an index of angular positions, and "mcs" refers to the mechanical or steering coordinate system 505 of the steering system 500. The extended calibrating act includes acquiring orientation data or information of the ICE catheter 130 at corresponding angular positions denoted as T(scs.a1 relative to wcs), T(scs.a2 relative to wcs) . . . to T(scs.an relative to wcs), where "scs" refers to the frame 510. The displacement or alignment T between the ICE imaging system 126 and the steering system 500 can be estimated through the following algorithms:

$$T(mcs \text{ relative to } scs) = \text{average}[T(mcs.ai \text{ relative to } wcs) - T(scs.ai \text{ relative to } wcs)],$$

where i=1, 2, . . . n, and where T(mcs relative to scs) represents the calibration information that is operable to be stored in the memory of the controller 210 or other computer readable medium and to communicate to the ICE imaging system 126.

A technical effect of the above-described system 100 and method 300 described above is an ability to calibrate a four dimensional, ICE catheter system 126 with a tracking system 125 via a frame 335, 510 of fiducials 330, 515 and computer readable program executions stored and executable at the controller 210. The controller 210 is operable to perform registration of the coordinate systems 320, 325, 505 relative to one another and the measured spatial relation and orientation of voxels of image data of the frame of fiducials 330, 515 as acquired by the ICE imaging system 126. Another technical effect of the system 100 and method 300 described above is an ability to calibrate the ICE imaging system 126 and tracking system 115 with the steering system 500 of the ICE catheter 130 or other tools 105. The system 100 also provides for tracking the position and orientation of the transducer array 132 at the ICE catheter 130, enhances superposition of the image data generated by the ICE imaging system 126 with other models generated by other imaging systems 128 (e.g., MRI, CT, PET, X-ray, Fluoroscopy, etc.), provides for navigation of the ICE catheter 130 or other tools 105 associated with ablation in combination with acquiring imaging data with the ICE imaging system 126, and tracking movement and orientation of the ICE catheter 130 or other tools 105 and synchronizing their movement with electrophysiological signals (e.g., respiratory cycle, cardiac cycle, etc.) as tracked by the electrophysiological system(s) 460.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A system to navigate in an area of interest of an imaged subject in relation to an acquired image of the imaged subject, comprising:
    an intracardiac echocardiography (ICE) imaging system having a transducer operable to acquire image data so as to create a four-dimensional image model of the imaged subject, the model defined in spatial relation and orientation relative to an image coordinate system;
    a tracking system operable to track movement and orientation of the transducer through the imaged subject relative to a tracking coordinate system; and
    a controller electrically connected in communication with the imaging system and the tracking system, the controller having a processor operable to execute a plurality of program instructions stored in a memory, the plurality of program instructions in combination with the processor operable to:
        register the image coordinate system with the tracking coordinate system; and
        calibrate the image coordinate system and the tracking coordinate system relative to a common reference having a plurality of fiducials of known spatial relation.

2. The system of claim 1, wherein the ICE imaging system includes a steering control system operable to drive movement of a tool relative to steering coordinate system, wherein the controller includes instructions to calibrate the steering coordinate system relative to the image coordinate system and to the tracking coordinate system.

3. The system of claim 2, wherein the common reference includes a docking station configured to receive the tool at a known location and orientation relative to the plurality of fiducials.

4. The system of claim 3, wherein the docking station includes an adapter configured such the tool can rotate along a longitudinal axis of the tool relative to the frame.

5. The system of claim 2, wherein the tool is part of a transducer operable to acquire the image data of the imaged subject.

6. The system of claim 5, wherein the transducer employs ultrasound to acquire the image data.

7. The system of claim 5, wherein a motor rotates the transducer about a longitudinal axis of the transducer.

8. The system of claim 7, wherein the motor changes a direction of rotation of the transducer about the longitudinal axis.

9. A method of navigating in an area of interest of an imaged subject, the method comprising the acts of:
    generating a four-dimensional model of the region of interest of the imaged subject with an intracardiac echocardiography (ICE) imaging system, the four-dimensional model including image data arranged in spatial relation and orientation relative to an image coordinate system and correlated relative to a time of acquisition;
    tracking movement and orientation of the transducer traveling through the imaged subject relative to a tracking coordinate system;
    registering the image coordinate system relative to the tracking coordinate system; and
    calibrating the image coordinate system and the tracking coordinate system relative to a common reference frame comprising a plurality of fiducials of known spatial relation.

10. The method of claim 9, further including the act of:
    directing movement of the transducer via a steering control system relative to steering coordinate system; and
    calibrating the steering coordinate system relative to the image coordinate system and to the tracking coordinate system.

11. The method of claim 9, wherein the common reference includes a docking station configured to receive the transducer at a known location and orientation relative to the plurality of fiducials.

12. The method of claim 11, further including the act of:
    rotating the transducer along a longitudinal axis of the transducer relative to the frame.

13. The method of claim 9, wherein the transducer is part of a tool traveling through the imaged subject.

14. The method of claim 9, wherein the transducer employs ultrasound to acquire the image data, and further including the act of acquiring ultrasound image data of the plurality of fiducials.

15. The method of claim 14, wherein a motor rotates the transducer about a longitudinal axis of the transducer.

16. The method of claim 15, wherein the motor changes a direction of rotation of the transducer about the longitudinal axis.

17. The method of claim 9, further including the act of:
    calculating the location and orientation of the plurality of fiducials relative to the common reference frame.

18. A frame to calibrate an imaging system relative to a tracking system, the imaging system including a transducer operable to acquire image data of an imaged subject, comprising:
    a plurality of fiducials of known spatial relation relative to one another; and an adapter configured to receive the transducer of the imaging system, the adapter configured to rotate with respect to the frame, wherein the imaging system is an intracardiac echocardiography (ICE) imaging system, the transducer employs ultrasound to acquire image data of the imaged subject, and the plurality of fiducials are compatible to be detected with ultrasound.

19. The frame of claim 18, wherein the adapter is configured such that the transducer rotates about a longitudinal axis of the transducer.

* * * * *